(12) United States Patent
Wilson

(10) Patent No.: US 10,342,525 B2
(45) Date of Patent: Jul. 9, 2019

(54) BREAST RETRACTOR TOOL

(71) Applicant: Wesley Wilson, Scottsdale, AZ (US)

(72) Inventor: Wesley Wilson, Scottsdale, AZ (US)

( * ) Notice: Subject to any disclaimer, the term of this patent is extended or adjusted under 35 U.S.C. 154(b) by 205 days.

(21) Appl. No.: 15/495,694

(22) Filed: Apr. 24, 2017

(65) Prior Publication Data

US 2017/0303905 A1   Oct. 26, 2017

Related U.S. Application Data

(60) Provisional application No. 62/326,725, filed on Apr. 23, 2016.

(51) Int. Cl.
*A61B 17/02* (2006.01)
*A61B 17/00* (2006.01)

(52) U.S. Cl.
CPC .... *A61B 17/02* (2013.01); *A61B 2017/00796* (2013.01)

(58) Field of Classification Search
CPC ............... A61B 17/02; A61B 2017/00796
See application file for complete search history.

(56) References Cited

U.S. PATENT DOCUMENTS

| | | | | |
|---|---|---|---|---|
| 2,648,329 A | * | 8/1953 | Trier | A61B 1/267 600/193 |
| 3,766,909 A | * | 10/1973 | Ozbey | A61B 1/07 385/117 |
| 2002/0001202 A1 | * | 1/2002 | Williams | A61B 17/02 362/572 |

* cited by examiner

*Primary Examiner* — Christian A Sevilla
(74) *Attorney, Agent, or Firm* — Intellectual Strategies

(57) ABSTRACT

Embodiments of a breast implant retractor tool are described. Some embodiments of a breast implant retractor tool allow for the accurate placement of breast implants with zero or minimal air trapped in the breast implant cavity. In one embodiment, a surgical retractor tool includes a handle and a blade. The blade is connected to and extends away from the handle. The blade includes an internal pathway which defines a passageway from a first opening or inlet on the blade to a second opening or outlet.

18 Claims, 7 Drawing Sheets

BREAST RETRACTOR TOOL

BACKGROUND

Breast implants are sometimes placed to enhance the size and/or shape of a woman's breasts in elective surgery. In addition, breast implants are sometimes necessary for reconstructive surgery following breast cancer. Such procedures include utilizing tools to allow a surgeon to place the implant within a cavity within the cavity.

Breast implants are inserted into a cavity through a small opening or incision in the breast. As the implant may be larger than the opening through which the implant is inserted, the implant may effectively seal off the opening and prevent air trapped inside the breast tissue from exiting through the incision. In this way, the air is trapped behind the implant, or on the opposite side of the implant from the incision. Excess air within the cavity is detrimental to the accurate placement of the implant as well as the stability of the implant.

SUMMARY

Embodiments of a breast implant retractor tool are described. Some embodiments of a breast implant retractor tool allow for the accurate placement of breast implants with zero or minimal air trapped in the breast implant cavity. In one embodiment, a surgical retractor tool includes a shaft, a handle, a blade extension, and an internal pathway. The handle is disposed at a first end of the shaft. The blade extension disposed at a second end of the shaft opposite the handle forming a heel between the shaft and the blade extension. In some embodiments, the blade extension extends away from the shaft at an angle between about 45 degrees and about 135 degrees. The internal pathway extends internally from a first opening on the blade to a second opening on the shaft. The first opening and the second opening are connected by an internal passageway through a first distance of the blade extension, the heel, and a second distance of the shaft.

In another embodiment, a surgical retractor tool includes a handle and a blade. The blade is connected to and extends away from the handle. The blade includes an internal pathway which defines a passageway from a first opening or inlet on the blade to a second opening or outlet.

In another embodiment, a surgical retractor tool includes insertion means, leveraging means, and venting means. The insertion means provide structure to facilitate insertion through an incision into breast tissue. The leveraging means provide a structure for applying a leveraging force to the insertion means, while inserted through the incision into the breast tissue, to stretch the incision to accommodate insertion of a pliable breast implant within a cavity of the breast tissue. The venting means are defined within at least the insertion means to facilitate evacuation of air or fluid trapped within the cavity of the breast tissue when the breast implant blocks passage of the air or fluid through the incision.

Other embodiments of the breast implant retractor tool and methods are also described. Other aspects and advantages of embodiments of the present invention will become apparent from the following detailed description, taken in conjunction with the accompanying drawings, illustrated by way of example of the principles of the invention.

DETAILED DESCRIPTION

Figure 1:
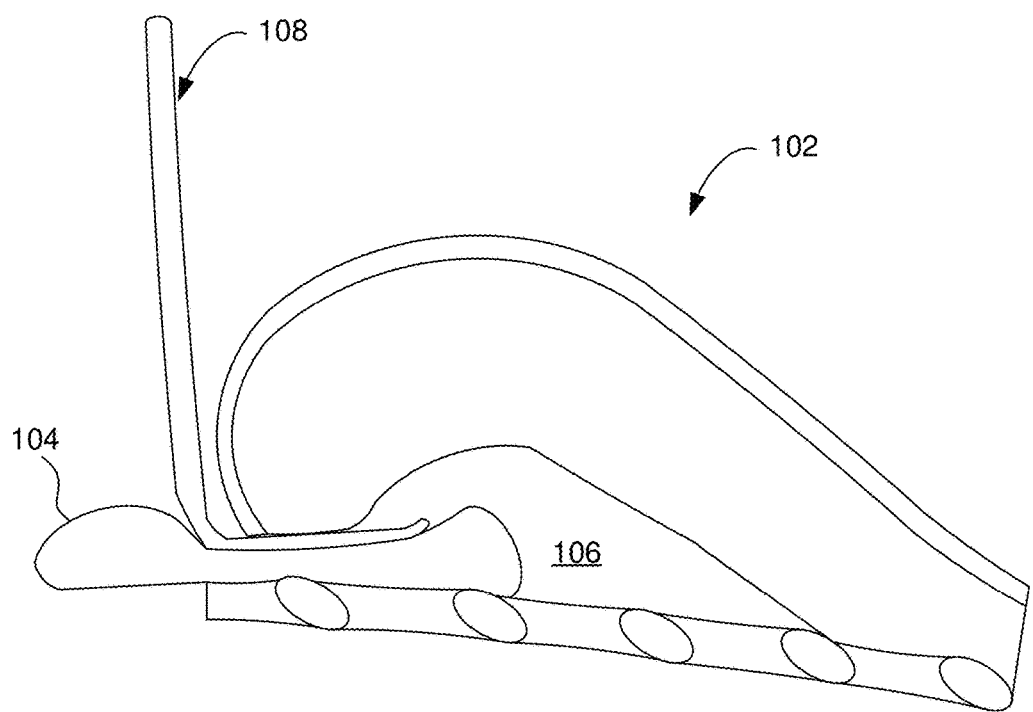
FIG. 1 depicts a schematic diagram of one embodiment of a retractor tool to aid with insertion of an implant into a breast cavity.

It will be readily understood that the components of the embodiments as generally described herein and illustrated in the appended figures could be arranged and designed in a wide variety of different configurations. Thus, the following more detailed description of various embodiments, as represented in the figures, is not intended to limit the scope of the present disclosure, but is merely representative of various embodiments. While the various aspects of the embodiments are presented in drawings, the drawings are not necessarily drawn to scale unless specifically indicated.

The present invention may be embodied in other specific forms without departing from its spirit or essential characteristics. The described embodiments are to be considered in all respects only as illustrative and not restrictive. The scope of the invention is, therefore, indicated by the appended claims rather than by this detailed description. All changes which come within the meaning and range of equivalency of the claims are to be embraced within their scope.

Reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussions of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize, in light of the description herein, that the invention can be practiced without one or more of the specific features or advantages of a particular embodiment. In other instances, additional features and advantages may be recognized in certain embodiments that may not be present in all embodiments of the invention.

Reference throughout this specification to "one embodiment," "an embodiment," or similar language means that a particular feature, structure, or characteristic described in connection with the indicated embodiment is included in at least one embodiment of the present invention. Thus, the phrases "in one embodiment," "in an embodiment," and similar language throughout this specification may, but do not necessarily, all refer to the same embodiment.

While many embodiments are described herein, at least some of the described embodiments allow for a breast retractor tool that allows for the removing of trapped air behind a breast implant during the implantation of the breast implant. Some embodiments of a breast retractor tool include an interior pathway that extends from the foot of the tool to the handle.

FIG. 1 depicts a schematic diagram of one embodiment of a retractor tool 108 to aid with insertion of an implant 104 into a breast cavity 106 of a breast 102. The retractor tool 108 is utilized to expand an opening or incision made on or near the breast. The implant 104 is inserted through the expanded opening or slit. Many times when the implant 104 is inserted through the opening, air is trapped within the cavity behind the implant 104. As the incision and the implant 104 are typically flexible, the skin at the incision will form a seal around the implant 104 and prevent air within the cavity 106 from escaping. Additionally, the tissue within the breast similarly can form a seal around the implant 104 to form a seal and trap air within the cavity 106. This presents a difficulty in the insertion of the implant 104 into the cavity 106 because the trapped air cannot escape past the implant 104, and the implant 104 cannot be fully inserted into the cavity 104 because of the pocket of trapped air. Thus, the trapped air should be expelled so that the implant 104 can be fully inserted into the cavity 106. Also, the presence of excess air in the cavity 106 may be detrimental to the functioning and stability of the inserted implant 104. As such it is beneficial to release the trapped air from the cavity 106 in order for the implant 104 to fit as designed.

Embodiments of the invention allow for the trapped air to escape through a pathway within the retractor tool 108. In some embodiments, the pathway has an opening or inlet at a first end on the retractor tool 108. The first end is the end of the retractor tool that is inserted into the cavity 106. In some embodiments, the pathway extends internally through the retractor tool 108 to an opening or outlet at a portion of the handle of the retractor tool 108. In other embodiments, the pathway does not extend all the way to the handle of the retractor tool 108, but extends sufficiently far to allow the outlet to be located outside the cavity 106. Thus, the second opening may be located on a lower portion of the retractor tool 108, for example at about the "heel" of the retractor tool 108 or on the lower shaft of the retractor tool 108.

Figure 2:
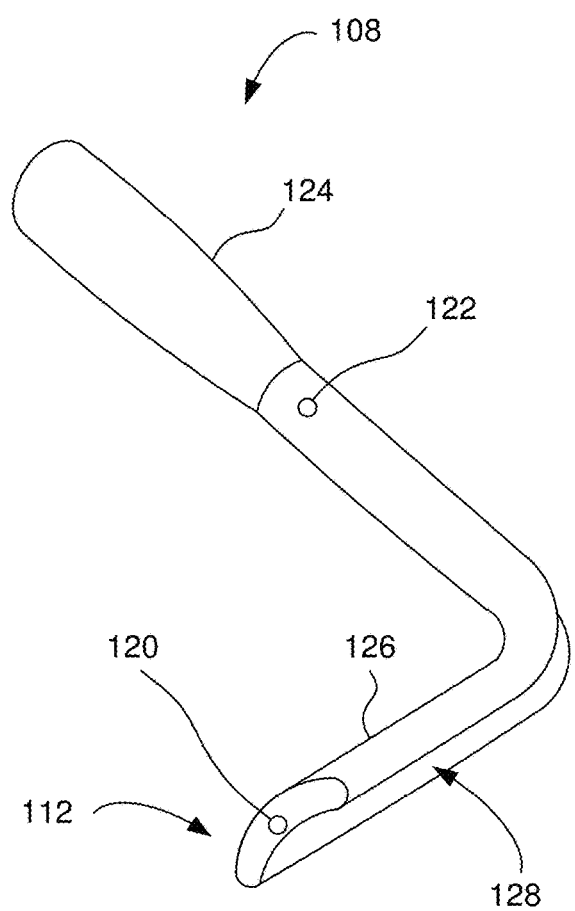
FIG. 2 depicts a perspective view of an embodiment of the breast retractor tool of FIG. 1.

FIG. 2 depicts a perspective view of an embodiment of the breast retractor tool 108 of FIG. 1. Although the retractor tool 108 is shown and described with certain components and functionality, other embodiments of the retractor tool 108 may include fewer or more components to implement less or more functionality.

In the illustrated embodiment, the retractor tool 108 includes an integral blade (although not for cutting) or extension 126 and a handle portion 124. In some embodiments, the extension 126 is the portion of the retractor tool 108 that is inserted through the opening in a breast and is used to lift the breast and expand the opening in order for the implant 104 to be inserted through the opening. In some embodiments, the retractor tool 108 is a solid piece with an internal air pathway.

In the illustrated embodiment, the pathway begins at a first opening or inlet 120 at a first end 112 of the retractor tool 108. In the illustrated embodiment the pathway is a cavity that extends from the first opening through the integral blade 126 of the retractor tool 108 and up through part of the handle portion 124 of the retractor tool to a second opening or outlet 122. When the retractor tool 108 is used, the first opening 120 is at a position that is inserted into the cavity 106 of a breast 102. The first opening 120 is exposed to the trapped air within the cavity 106. The pathway is internal to the retractor tool 108 and will provide a pathway for the trapped air to travel through the retractor tool 108 to the second opening 122. The second opening 122 is at a portion of the retractor tool 108 that is exposed to the ambient environment outside the breast 102. As the implant 104 is inserted through the opening air within the cavity behind the implant 104 will be forced through the path and out the second opening 122.

Although not shown, other embodiments may have multiple inlets and/or multiple outlets. An embodiment having two or more inlets spaced apart from one another may allow air to pass through one of the inlets even if the other inlet is blocked by tissue or the implant 104. In some embodiments, at least two inlets are located on opposite surfaces (i.e., top and bottom) of the blade 126. In other embodiments, at least one of the inlets may be located on a lip or edge or the blade 126.

Figure 3:
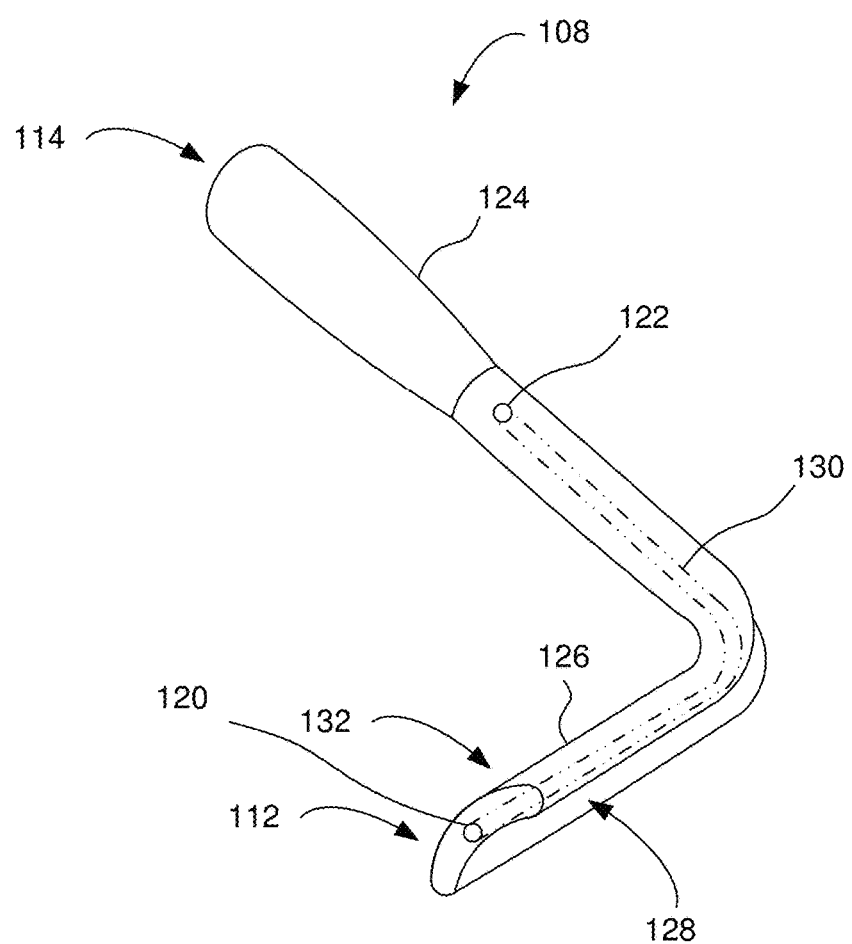
FIG. 3 depicts another perspective view of the breast retractor tool of FIG. 1, including an indication of the interior pathway to allow air to pass from the inlet to the outlet.

FIG. 3 depicts a perspective view of the breast retractor tool of FIG. 1, including an indication of the interior pathway to allow air to pass from the inlet to the outlet. As is depicted in FIG. 3, the pathway 130 is internal to the retractor tool 108 and extends from the first opening 120 to the second opening 122. As is depicted, the pathway 130 extends through the integral blade 126 and up through a handle portion 124 of the retractor tool 108. The first opening 120 and the second opening 122 may be positioned in various locations on the retractor tool 108. In some embodiments, the first opening 120 is positioned at a farthest point on a first end 112 of the retractor tool. In some embodiments, the first opening 120 is positioned on a top side 132 of the integral blade 126 of the retractor tool 108. In some embodiments, the first opening 120 is positioned on a bottom side 128 of the integral blade 126 of the retractor tool 108.

In some embodiments, the second opening 122 is positioned on the handle portion 124 of the retractor tool 108. In the illustrated embodiment the second opening 122 is positioned halfway up the handle portion 124 of the retractor tool 108. In some embodiments, the pathway 130 extends all the way through the handle portion 124 and the second opening 122 is positioned at a second end 114 of the retractor tool 108. In some embodiments the second opening 122 is positioned at a location where the handle portion 124 and the integral blade 126 meet. The second opening 122 may be positioned on the back, front, side, or top of the handle portion 124 of the retractor tool 108. In some embodiments the first opening 120 and the second opening 122 have the same shape and size. In some embodiments, the pathway increases in cross-sectional area from the first opening 120 to the second opening 122. In some embodiments, the pathway decreases in cross-sectional area from the first opening 120 to the second opening 122.

In a further embodiment, the pathway and/or the outlets 122 may be shaped to generate a certain tone or noise profile upon passage of air through the passage and/or the outlet 122. For example, the outlet may be shaped to form a whistle, or to generate a whistle sound at a specific pitch (or within a range of pitches) so that the outlet 122 can provide specific audible feedback to the doctor using the retractor tool 108. In further embodiments, an attachment may be disposed at the outlet to assist with the generation of the audible feedback from the outlet 122. In other embodiments, other types airflow monitoring and/or feedback aids may be implemented for visual, tactile, and/or audible responses to passage of air through the pathway and/or the outlet 122.

The retractor tool 108 may take various shapes. In the illustrated embodiment, the top surface 132 of the integral blade 126 is convex and the bottom surface 128 of the integral blade 126 is concave. In some embodiments, the top surface 132 and/or bottom surface 128 may be flat. In some embodiments, the pathway forms one or more ridges on a surface of the integral blade 126 of the retractor tool 108.

Some embodiments may include more than one pathway. For example, embodiments may include two openings or inlets 120 on the integral blade 126 and two openings or outlets 122 on the handle portion 124, and separate pathways between pairs of inlets/outlets. Such an embodiment allows the retractor tool 108 to function properly even if one of the pathways is obstructed or otherwise blocked. In other embodiments, a single opening may connect with multiple internal pathways, and vice versa.

Figure 4:
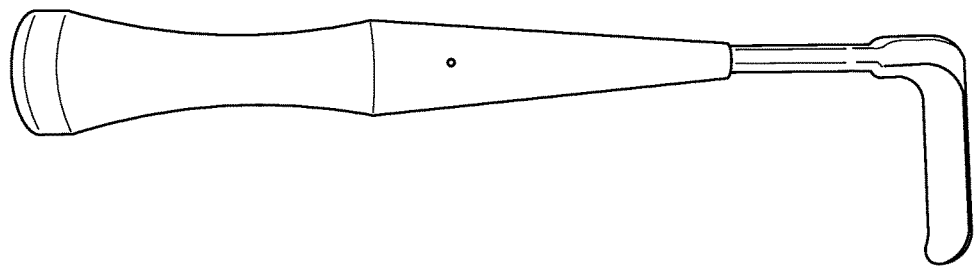
FIG. 4 depicts a side view of one embodiment of a first prototype of a breast retractor tool.

FIG. 4 depicts a side view of one embodiment of a first prototype of a breast retractor tool. The illustrated embodiment depicts a handle portion and an integral blade. The integral blade is the part of the tool that is inserted through the opening in a breast and used to lift the breast and expand the opening in order for the implant to be inserted through the opening. In some embodiments the retractor tool is a solid piece with an internal pathway extending from a first end of the retractor tool to a second end of the retractor tool.

Figure 5:
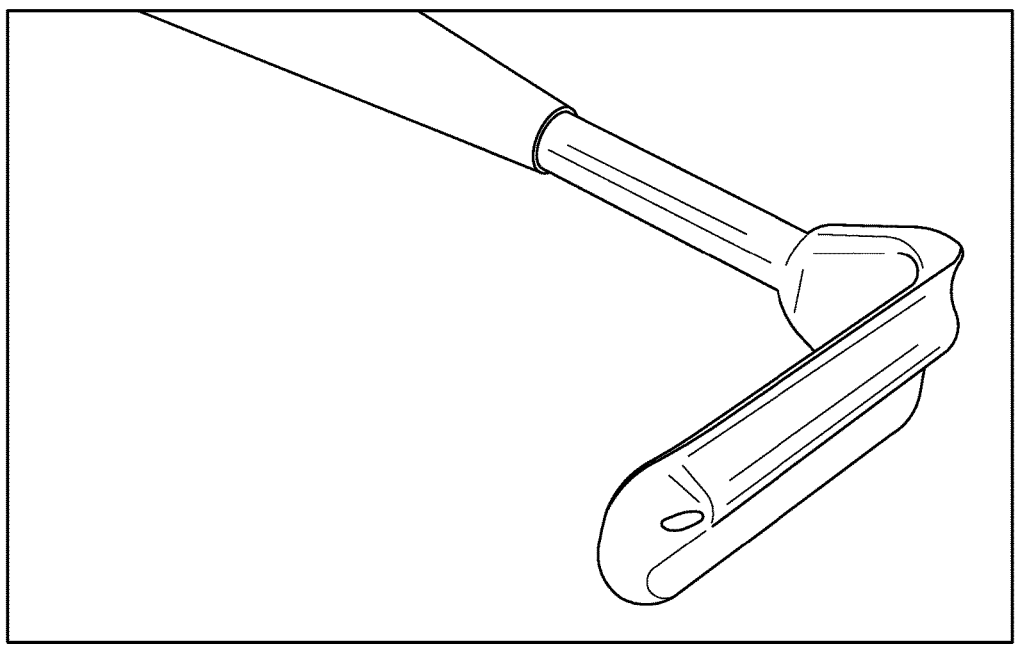
FIG. 5 depicts a view of the bottom of the first prototype of the breast retractor tool, showing an inlet integrated into the contour of the retractor tool.

FIG. 5 depicts a view of the bottom of the first prototype of the breast retractor tool, showing an inlet integrated into the contour of the retractor tool. The depicted view shows a first opening or inlet on the bottom surface of the integral blade of the retractor tool. To accommodate the internal pathway, the bottom surface of the blade forms a central ridge of integral blade. In other embodiments, the ridge may be located on one side or the other of the blade. Alternatively, the outside surfaces of the blade may show no features corresponding to the location of the internal pathway.

Figure 6:
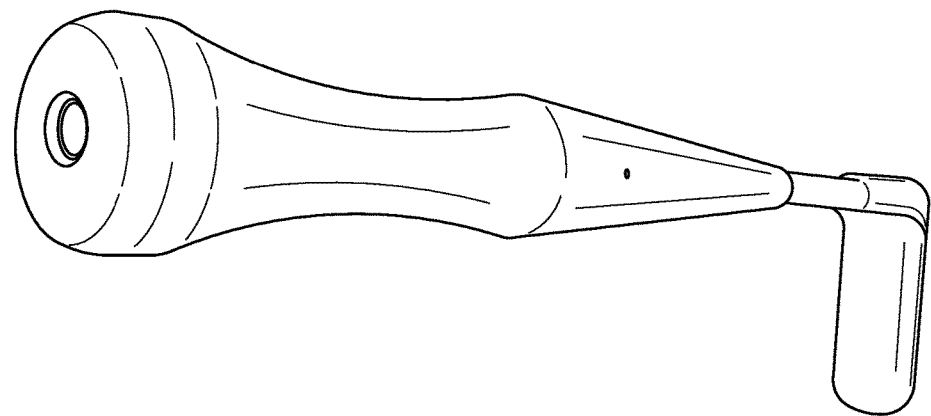
FIG. 6 depicts a view of the top of the first prototype of the breast retractor tool, showing an outlet integrated into the handle of the retractor tool.

FIG. 6 depicts a view of the top of the first prototype of the breast retractor tool, showing an outlet integrated into the handle of the retractor tool. The depicted embodiment shows a second opening or outlet on the top of the handle portion of the retractor tool. Although the exact location of the outlet may not be critical in some embodiments, it is useful for the outlet to be located in a position that is not likely to be covered or obstructed by the doctor's hands or other materials during use of the retractor tool.

Figure 7:
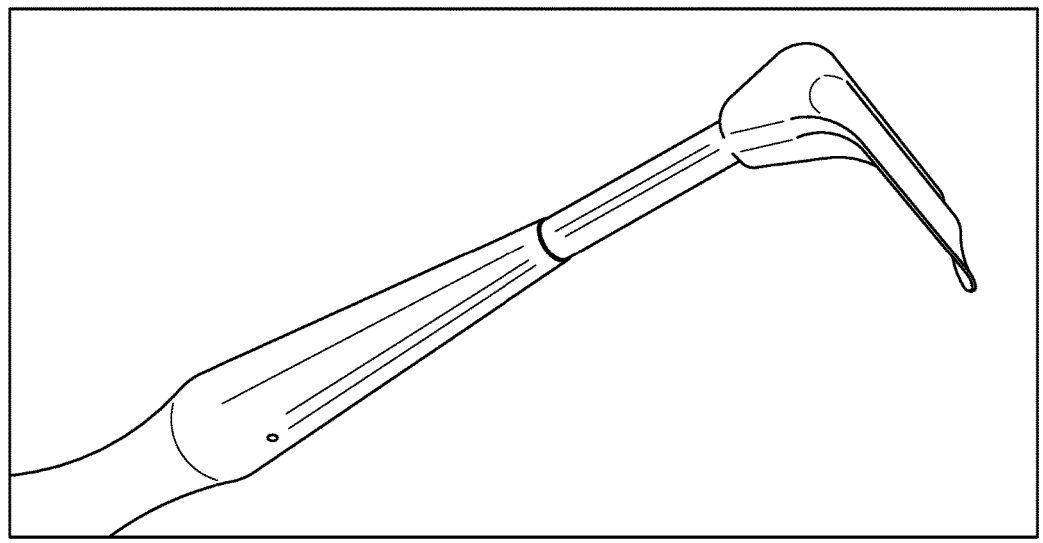
FIG. 7 depicts a perspective view of the first prototype of the breast retractor tool.

FIG. 7 depicts a perspective view of the first prototype of the breast retractor tool. The depicted embodiment shows the ridge formed along the bottom side of the integral blade of the retractor tool. The pathway extends internally along the length of the handle and shaft, although other embodiments may include one or more outlets along the lateral sides of the handle or shaft.

Figure 8:
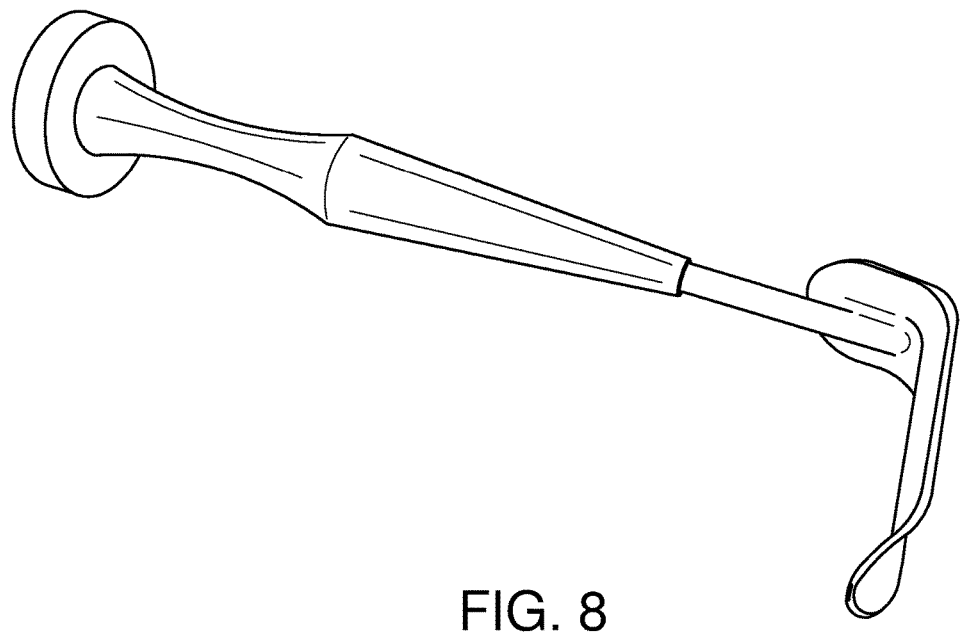
FIG. 8 depicts a perspective view of one embodiment of a second prototype of a breast retractor tool, showing an inlet integrated into the contour of a lip of the retractor tool.

FIG. 8 depicts a perspective view of one embodiment of a second prototype of a breast retractor tool, showing an inlet integrated into the contour of a lip of the retractor tool. Additionally, in the depicted embodiment, the front lip or edge of the blade is inclined upward from the general extension direction of the blade. In an alternative embodiment the tip may be inclined in a different direction. Rather than being located on the bottom surface of the blade, the inlet in the depicted embodiment may be easier to maneuver based on the ability to tip the tool toward and away from the breast, thereby moving the tip of the blade and the integrated inlet within the breast cavity.

Figure 9:
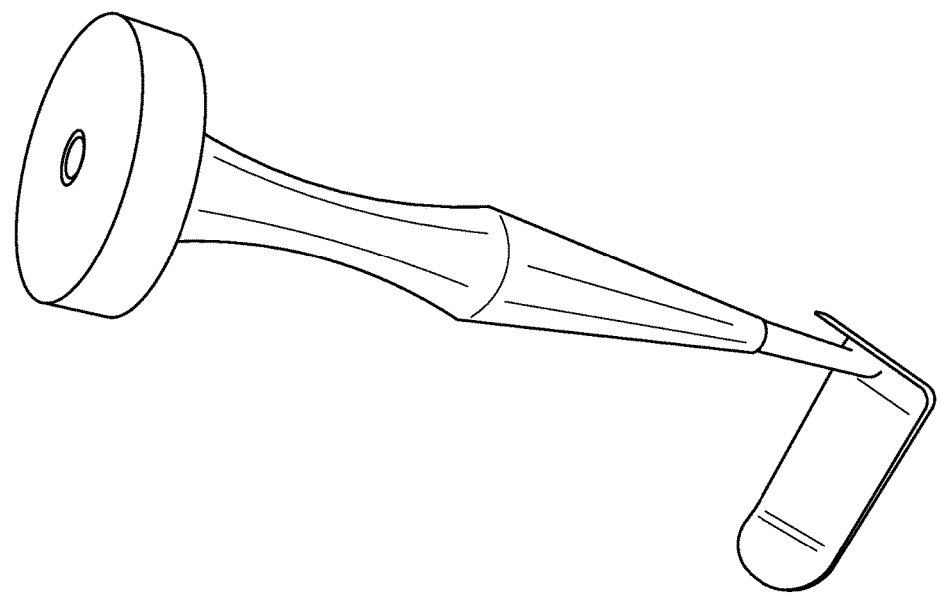
FIG. 9 depicts a view of the top of the second prototype of the breast retractor tool, showing an outlet integrated into the handle of the retractor tool.

FIG. 9 depicts a view of the top of the second prototype of the breast retractor tool, showing an outlet integrated into the handle of the retractor tool. This is similar in many ways to the embodiment shown in FIG. 6.

Figure 10:
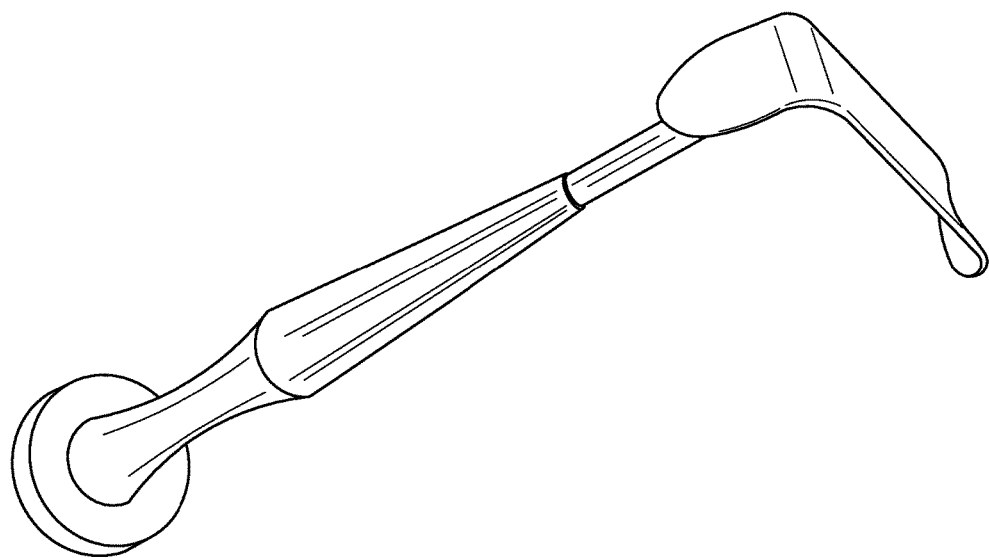
FIG. 10 depicts a perspective view of the second prototype of the breast retractor tool.

FIG. 10 depicts a perspective view of the second prototype of the breast retractor tool. This is similar in many ways to the embodiment shown in FIG. 7.

Figure 11:
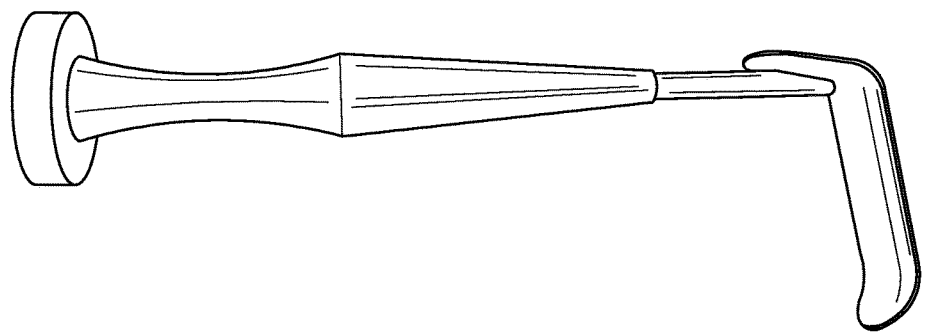
FIG. 11 depicts a side view of the second prototype of the breast retractor tool.

FIG. 11 depicts a side view of the second prototype of the breast retractor tool. This is similar in many ways to the embodiment shown in FIG. 4.

The embodiment of the second prototype shown in FIGS. 8-11 has a different shape for the blade, extension, or foot of the retractor tool. In embodiments with a similar shape, the outlet may be located on a back surface or edge of the blade, for example somewhere on the portion of the blade that extends more or less in the same general direction as the shaft and handle.

In further embodiments, parts of the retractor tool may be modular, so that pieces can be assembled together or disassembled into separate pieces. For example, in some embodiments, the blade portion may include the entire internal pathway and the inlet and outlet, and the blade portion may be detachable from the shaft and handle portions, as long as the assembled pieces have sufficient structural integrity to facilitate the forces necessary for manipulation of the skin, tissue, and implant during the implantation procedure.

In further embodiments, a surgical retractor tool includes a shaft, a handle, a blade extension, and an internal pathway. The handle is disposed at a first end of the shaft. The blade extension disposed at a second end of the shaft opposite the handle forming a heel between the shaft and the blade extension. In some embodiments, the blade extension extends away from the shaft at an angle between about 45 degrees and about 135 degrees. The internal pathway extends internally from a first opening on the blade to a second opening on the shaft. The first opening and the second opening are connected by an internal passageway through a first distance of the blade extension, the heel, and a second distance of the shaft. The first opening may be located in one of many locations on the blade extension. For example, the first opening is may be located on a distal edge of the blade extension at a maximum distance from the heel, as in FIGS. 2, 3, and 8. In another example, the first opening is located on an underside of the blade extension, as in FIG. 5. In another example, multiple opening may be used, and the openings may connect to one another internally and to the second opening. In another example, the first opening is at least partially located on a concave surface of the blade extension, as in FIG. 5. Also, in some embodiments, the blade extension has a flared tip in which a distal tip of the blade extension is flared in a direction which opens the concave surface of the blade extension, as in the various embodiments shown in FIGS. 4-11. Similarly, in some embodiment, the heel is rounded upward toward the shaft, as in the various embodiments shown in FIGS. 4-11. In other embodiments, the internal passageway may be offset within the blade extension to run internally along a side of the blade extension. In this way, as compared with the embodiments shown in FIGS. 4-7, the outer form of the passageway might be kept to one side or the other of a concave underside of the retractor tool.

In another embodiment, a surgical retractor tool includes a handle and a blade. The blade is connected to and extends away from the handle. The blade includes an internal pathway which defines a passageway from a first opening or inlet on the blade to a second opening or outlet. In further embodiments, the second opening or outlet may be disposed on another surface of the blade which is located a distance away from the first opening or inlet. Alternatively, the second opening or outlet is disposed on a shaft of the handle. In a specific example, the second opening or outlet is located at a distal end of the handle, opposite the side to which the blade is coupled. In another embodiment, the first opening or inlet is located on a lip or edge of the blade.

In another embodiment, a surgical retractor tool includes insertion means, leveraging means, and venting means. The insertion means provide structure to facilitate insertion through an incision into breast tissue. The leveraging means provide a structure for applying a leveraging force to the insertion means, while inserted through the incision into the breast tissue, to stretch the incision to accommodate insertion of a pliable breast implant within a cavity of the breast tissue. The venting means are defined within at least the insertion means to facilitate evacuation of air or fluid trapped within the cavity of the breast tissue when the breast implant blocks passage of the air or fluid through the incision. In one embodiment, the venting means includes inlet means disposed on the insertion means to facilitate the air or fluid entering the venting means through the inlet means from the cavity in the breast tissue. In another embodiment, the inlet means are further disposed on the insertion means at a location that is maneuverable by the leveraging means applying the leveraging force on the insertion means. In other words, by moving the handle of the tool, the blade and, consequently, the inlet on the blade move in a corresponding manner. In another embodiment, the venting means includes outlet means disposed on the insertion means to facilitate the air or fluid exiting the cavity of the breast tissue and the venting means through outlet means. In another embodiment, the venting means includes outlet means disposed on the leveraging means to facilitate the air or fluid exiting the cavity of the breast tissue and the venting means through outlet means. In another embodiment, the venting means includes outlet means disposed on the insertion means to facilitate the air or fluid exiting the cavity of the breast tissue and the venting means through outlet means. In another embodiment, the insertion means further includes external channeling means, such as a concave surface, to accommodate and direct movement of the breast implant past the insertion means and through the incision into the cavity of the breast tissue.

In the above description, specific details of various embodiments are provided. However, some embodiments may be practiced with less than all of these specific details. In other instances, certain methods, procedures, components, structures, and/or functions are described in no more detail than to enable the various embodiments of the invention, for the sake of brevity and clarity.

Although the operations of the method(s) herein are shown and described in a particular order, the order of the operations of each method may be altered so that certain operations may be performed in an inverse order or so that certain operations may be performed, at least in part, concurrently with other operations. In another embodiment, instructions or sub-operations of distinct operations may be implemented in an intermittent and/or alternating manner.

Although specific embodiments of the invention have been described and illustrated, the invention is not to be limited to the specific forms or arrangements of parts so described and illustrated. The scope of the invention is to be defined by the claims appended hereto and their equivalents.

What is claimed is:

1. A surgical retractor tool comprising:
   a shaft;
   a handle disposed at a first end of the shaft;
   a blade extension disposed at a second end of the shaft opposite the handle forming a heel between the shaft and the blade extension, wherein the blade extension extends away from the shaft at an angle between about 45 degrees and about 135 degrees; and
   an internal pathway which extends internally from at least one first opening on the blade to a second opening on the shaft, wherein the at least one first opening and the second opening are connected by an internal passageway through a first distance of the blade extension, the heel, and a second distance of the shaft.

2. The surgical retractor tool of claim 1, wherein the at least one first opening is disposed on a distal edge of the blade extension at a maximum distance from the heel.

3. The surgical retractor tool of claim 1, wherein the at least one first opening is disposed on an underside of the blade extension.

4. The surgical retractor tool of claim 1, wherein the at least one first opening comprises at least two openings on at least one surface of the blade extension.

5. The surgical retractor tool of claim 1, wherein the at least one first opening is at least partially disposed on a concave surface of the blade extension.

6. The surgical retractor tool of claim 5, wherein the blade extension comprises a flared tip in which a distal tip of the blade extension is flared in a direction which opens the concave surface of the blade extension.

7. The surgical retractor tool of claim 5, wherein the heel is rounded upward toward the shaft.

8. The surgical retractor tool of claim 1, wherein the internal passageway is offset within the blade extension to run internally along a side of the blade extension.

9. A surgical retractor tool comprising:
   a handle; and
   a blade connected to and extending away from the handle, wherein the blade comprises an internal pathway which defines a passageway from a first opening or inlet on the blade to a second opening or outlet.

10. The surgical retractor tool of claim 9, wherein the second opening or outlet is disposed on another surface of the blade which is located a distance away from the first opening or inlet.

11. The surgical retractor tool of claim 9, wherein the second opening or outlet is disposed on a shaft of the handle.

12. The surgical retractor tool of claim 11, wherein the second opening or outlet is disposed at a distal end of the handle, opposite the side to which the blade is coupled.

13. The surgical retractor tool of claim 9, wherein the first opening or inlet is located on a lip or edge of the blade.

14. A surgical retractor tool comprising:
   insertion means for insertion through an incision into breast tissue;
   leveraging means for applying a leveraging force to the insertion means, while inserted through the incision into the breast tissue, to stretch the incision to accommodate insertion of a pliable breast implant within a cavity of the breast tissue; and venting means defined within at least the insertion means to facilitate evacuation of air or fluid trapped within the cavity of the breast tissue when the breast implant blocks passage of the air or fluid through the incision;

wherein the venting means comprises outlet means disposed on the insertion means to facilitate the air or fluid exiting the cavity of the breast tissue and the venting means through outlet means.

15. The surgical retractor tool of claim 14, wherein the venting means comprises inlet means disposed on the insertion means to facilitate the air or fluid entering the venting means through the inlet means from the cavity in the breast tissue.

16. The surgical retractor tool of claim 15, wherein the inlet means are further disposed on the insertion means at a location that is maneuverable by the leveraging means applying the leveraging force on the insertion means.

17. The surgical retractor tool of claim 14, wherein the venting means comprises outlet means disposed on the leveraging means to facilitate the air or fluid exiting the cavity of the breast tissue and the venting means through outlet means.

18. The surgical retractor tool of claim 14, wherein the insertion means further comprises external channeling means to accommodate and direct movement of the breast implant past the insertion means and through the incision into the cavity of the breast tissue.

* * * * *